United States Patent [19]

Allison et al.

[11] Patent Number: 4,460,370
[45] Date of Patent: Jul. 17, 1984

[54] TRANS-DERMAL MEDICATION APPLICATION CELL

[75] Inventors: Kenneth C. Allison, Crystal Lake; Roger D. Allison, Bensenville; Charlotte C. Allison, Crystal Lake, all of Ill.

[73] Assignee: Almedco, Inc., Crystal Lake, Ill.

[21] Appl. No.: 450,559

[22] Filed: Dec. 16, 1982

Related U.S. Application Data

[63] Continuation of Ser. No. 316,347, Oct. 29, 1981, abandoned.

[51] Int. Cl.³ .............................................. A61M 7/00
[52] U.S. Cl. ..................................... 604/897; 128/156
[58] Field of Search ............... 604/896, 897, 304, 305, 604/307; 128/155, 156

[56] References Cited

U.S. PATENT DOCUMENTS

| | | | |
|---|---|---|---|
| 3,367,332 | 2/1968 | Groves | 128/156 |
| 3,550,589 | 12/1970 | Wallerstein | 128/156 |
| 3,742,951 | 7/1973 | Zaffaroni | 604/304 |
| 3,972,995 | 8/1976 | Tsuk et al. | 604/896 |
| 3,996,934 | 12/1976 | Zaffaroni | 604/896 |
| 4,055,672 | 10/1977 | Hirsch et al. | 426/127 |
| 4,117,842 | 10/1978 | Hutchins | 604/896 |
| 4,297,995 | 11/1981 | Golub | 604/304 |
| 4,309,996 | 1/1982 | Theeuwes | 604/896 |
| 4,379,454 | 4/1983 | Campbell et al. | 604/897 |

Primary Examiner—C. Fred Rosenbaum
Assistant Examiner—Sherri E. Vinyard
Attorney, Agent, or Firm—Jacque L. Meister

[57] ABSTRACT

A trans-dermal medication application cell for temporary attachment to the skin of a patient to facilitate the diffusion of medication solution from the cell's interior to the skin of a patient where it will be absorbed. A housing non-reactive with medication solutions is closed by a micro-porous diaphragm or membrane. A formed perforated medical foam sheet is secured to the housing and, in use, to the skin of a patient by a medical adhesive. A release sheet and vapor barrier secured to the foam sheet block exterior access to the micro-porous membrane and adhesive coated foam sheet prior to application to the patient's skin. A self locking and sealing plug closes the filling aperture in the housing in the principal invention embodiment.

19 Claims, 8 Drawing Figures

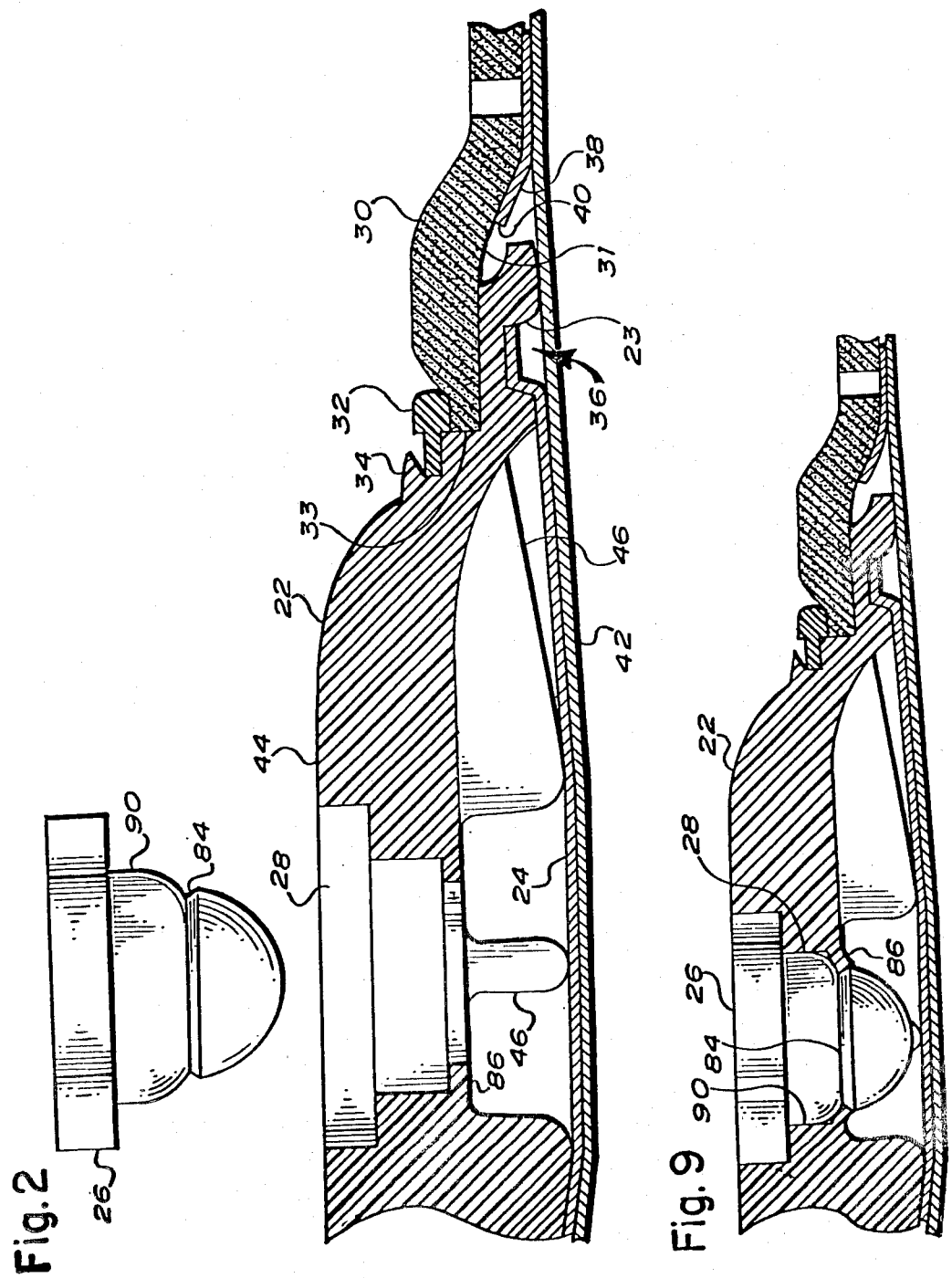

TRANS-DERMAL MEDICATION APPLICATION CELL

This application is a continuation of application Ser. No. 316,347, filed Oct. 29, 1981 now abandoned.

BACKGROUND OF THE INVENTION

This invention relates generally to medication application systems and more particularly to medication applicators adapted to dispense the medication contained in the interior of the medication applicator through a micro-porous film to and through the skin of a patient. This type of medication application system is sometimes characterized as a "trans-dermal application system".

Trans-dermal applications of medication are well known. In particular, Chandrasekaran in U.S. Pat. No. 4,201,211 describes a skin patch for delivering medication to the patient's skin where it is absorbed at a controlled rate which depends principally on the medication's concentration and the micro-porous membrane and its area which is in contact with skin. In this and other "bandage type" applications, the medication is dispersed in a carrier layer which alone or with a metering layer of micro-porous film, establishes medication flow rate to the skin. Because of the need for dispersion, the medication necessarily must be non-reactive with the carrier layer material and hence, requires different materials for the construction of the reservoir layer depending on the medication.

This non-uniformity in construction requires that the applicator be fabricated with the medication in place and this, in turn, causes problems with shelf life of the package since the medication is subject to deterioration as soon as the applicator is fabricated. Additionally, there are medications for which it is difficult or impossible to find a long lived compatible dispersing material. Further, the complete package is inherently fragile because of the fragile nature of the reservoir layer.

In other bandage type applicators, the medication material is carried as a liquid or gelatinous material in a reservoir. While it would appear that this type of construction would overcome the limitations of the above described bandage type applicators, those heretofore known have been difficult to fill and often subject to considerable lateral medication leakage with frequent secondary problems of staining of clothing or skin.

SUMMARY OF THE INVENTION

A principal object of the invention is to provide a new and improved trans-dermal medication application cell that overcomes the foregoing recited and other limitations of the prior art.

Still another object of the invention is to provide a new and improved trans-dermal medication application cell that is readily fillable with a wide variety of medications at high production rates.

Yet another object of the invention is to provide a new and improved trans-dermal medication application cell capable of separately holding plural medication compositions for simultaneous application at the same or dissimilar rates.

Another object of the invention is to provide a new and improved trans-dermal medication application cell bar and color codable to indicate the medication contents.

A further object of the invention is to provide a new and improved trans-dermal medication application cell that is capable of being filled by the prescriber or pharmacist supplier of the patient.

A still further object of the invention is to provide a new and improved trans-dermal medication application cell more comfortable in use than any heretofore known.

The foregoing and other objects of the invention are achieved in the preferred embodiment of the invention through use of a medication container closed on its skin contacting side by a micro-porous diaphragm the whole of which is surrounded by an annular, perforated foam, skin mounting medium. A release sheet and impermeable seal protect the contents of the medication container from contamination or leakage until the time of application. The nature of the invention and its several features and objects will appear more fully from the following description made in connection with the accompanying drawings.

BRIEF DESCRIPTION OF THE DRAWINGS

FIG. 2 is an enlarged view in cross-section of the trans-dermal application cell of the invention with portions broken away;

FIG. 9 is a view, similar to that of FIG. 2, showing the transdermal application cell with the retaining plug positioned to be locked in place and seal the cell.

DESCRIPTION OF THE PREFERRED EMBODIMENTS

Figure 1:
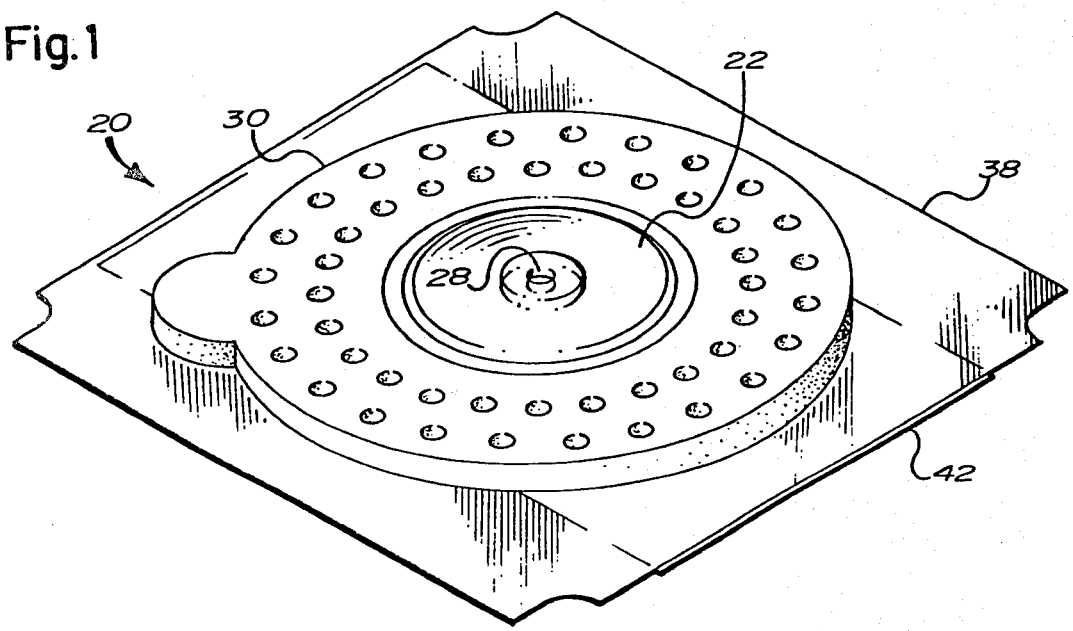
FIG. 1 is a perspective view of the trans-dermal application cell of the invention.
Figure 3:
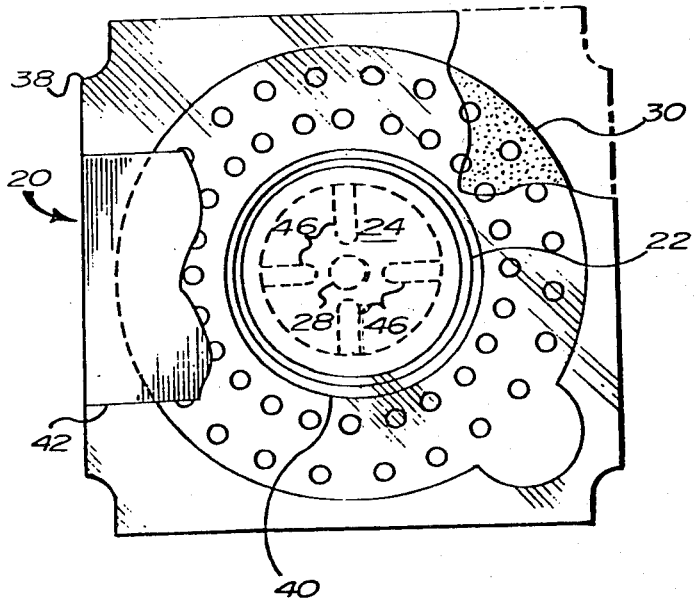
FIG. 3 is a bottom view of the application cell of FIG. 1 with portions of the release sheet and foil seal partially broken away to show details thereof.

FIGS. 1–3 illustrate the principal embodiment of the invention. In FIGS. 1 and 3 there are shown top and bottom views of the complete trans-dermal medication application cell at 20 with FIG. 2 being a cross-section thereof. A generally concave shaped housing 22 having an outwardly extending flange 23 at its periphery is closed on its open side by a micro-porous diaphragm or membrane 24 to form the medication container. The micro-porous membrane is advantageously secured to container 22 as by heat sealing in the area of the annular depression 36 in the flange 23 near the edge of the container. Because of this depressed location of the sealed edge, the somewhat rough edges of membrane 24 which might irritate a patient's skin are prevented from coming into skin contact when the cell is in use.

A retaining plug 26 inserted in housing 22 is used to close the filling aperture 28 in the housing after filling of the housing with a selected medication. A skin-adhering medical foam tape 30 is adhesively secured to flange 23 of housing 22 and mechanically secured thereto by retaining ring 32 which is, in turn, secured to housing 22 by hot staking at 34. Tape 30 is coated with medical adhesive 31 over its entire lower, skin-contacting, surface. A release sheet 38 is sealed to the foam tape by the same adhesive that is used to adhere the foam tape to the skin of a patient and prevents exposure of that adhesive before it is adhered to the skin. Advantageously, the release sheet 38 is coated with an adhesive release agent on the side toward the adhesive to reduce the tightness of the bond therebetween. The foam tape 30 has a central aperture 33. For manufacturing purposes since the foam tape 30 and release sheet 38 are advantageously fastened together before forming to the shapes shown, a central aperture 40 is formed in release sheet 38 at the same time aperture 33 is formed to permit direct contact of the micro-porous film with the patient's skin. The cell assembly is completed by a vapor barrier which advantageously is a 0.002 inch thick aluminum foil strip 42 having a commercial heat seal coating on one side which is heat sealed to the release sheet to block exterior access to the micro-porous membrane. This makes the complete cell airtight and, by preventing air or any other non-sterile material from contacting the micro-porous membrane and through it, the medication, thus preserves the medication in a sterile condition over a long shelf life.

The housing 22 is made relatively thick, on the order of between 0.040 inches and 0.100 inches with a median of 0.060 inches. This contrasts with an average thickness of 0.020 inches in other similar type applicators and this, in combination with the foil vapor barrier sealing strip 42, inhibits vapor transmission from the completed cell. As a result it is not unusual to achieve a 3 year minimum shelf-life for the medication filled cell of the invention whereas, prior art devices typically have a shelf-life of less than one year unless they are preserved in a sealed container.

As described above, retaining plug 26 is used to seal the filling aperture. Advantageously, plug 26 is of the same type described in the copending patent application of Kenneth C. Allison and William H. Cooley, Ser. No. 284824, for an Improved Blind Riveting and Sealing System. As there described and as shown in FIG. 9, rivet 26 is uniquely configured in combination with housing 22 and its filling aperture 28 to effect a tight seal and by flexing locking flange 86 into beveled locking groove 84, lock itself in position. As explained in the aforesaid copending application, the sealing action occurs both under the head 88 of plug 26 but also in the plug shank area of forcefit immediately under the head where it engages housing aperture 28. Further the plug 26 and filling aperture 28 are reciprocally configured so that the top surface 44 of the housing 22 is smooth with the plug in place. The housing 22 is advantageously constructed by molding from radiation resistant clear polypropylene which material is substantially chemically inert in the presence of most medication solutions.

It is a feature of the invention that the interior of housing 22 contains plural identical reinforcing ribs 46. These ribs depend generally away from the interior surface of the housing 22 and assist in supporting the micro-porous membrane in the open area over which it extends. Because of their tapered shape, the formation of air-pockets during filling is inhibited.

The micro-porous membrane 24 is of a commercially available type and, in the preferred embodiment, is 0.001 inches thick with a pore size of 0.02×0.2 micrometers and having a pore volume of substantially 38%. Pores of this size prevent bacterial transmission either from the cell interior to the skin or from the exterior to the interior of the cell. Other thicknesses, pore sizes and pore volumes may be used depending on the composition of the medication it is desired to accommodate.

As shown in FIGS. 1 and 2, the foam tape 30 is constructed with a stripping handle 48 for grasping when pulling off the release sheet 38 with foil strip 42. Tape 30 in the preferred embodiment is 1/16 inch thick white polyethylene closed cell foam. Because this material will be in contact with the patient's skin for at least several hours, a series of holes are cut into foam tape 30 to permit evaporation of moisture from the patient's skin. These apertures are shown as two concentric rings of holes the inner ring of which is at a radius greater than that of flange 23. These holes permit the skin to "breath".

It is a feature of the invention that release sheet 38 be high-density polyethylene 0.005" inches thick. This material has the combined desirable properties of toughness, and its ability to heat seal to the foil vapor barrier. Mylar has also been used for this application but is not preferred even though it is tougher, because of problems in adhering it to other materials.

Figure 8:
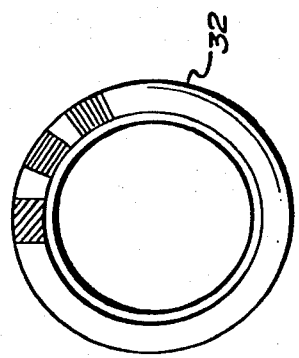
FIG. 8 is a plan view of the annular locking ring employed in the invention showing the bar and color coding used to identify the contents of the application cell of the invention.

It is a feature of the invention that retaining ring 32 can be color coded and/or otherwise marked to indicate the National Drug Code used by the pharmaceutical industry; color coding and other product or manufacturer designations being applied to the medication packages to lessen the possibility of administering the wrong material. Here, the ring can be bar color coded or other indicia applied, somewhat in the manner symbolically shown in FIG. 8 and achieve similar results. The marking of ring 32 is especially advantageous since the ring never is in contact with the patient or medication and hence the marking materials need not be medication compatible or non-allergic.

Figure 7:
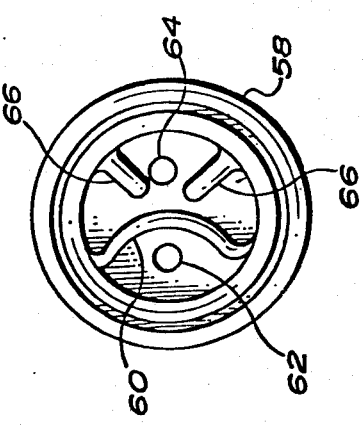
FIG. 7 illustrates an alternative construction of the medication container of FIG. 6.
Figure 6:
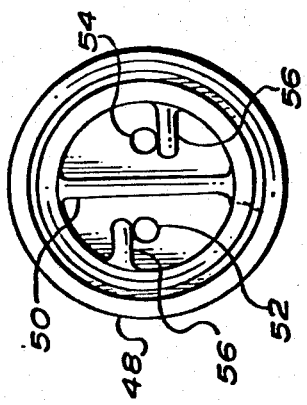
FIG. 6 is a view of a medication container embodiment used for simultaneous dispensing of 2 medications.

FIGS. 6 and 7 illustrate alternative configurations of the housing 22 shown in FIGS. 1-4. As best shown in FIGS. 2 and 3, the housing 22 comprises a cup-like single cavity construction. In the FIG. 6 configuration, the basic external shape of the housing 48 is identical to that of FIG. 1 but additionally, a dam 50 is inserted in the interior of the housing cavity dividing the cavity into two substantially identical volume compartments. Each of these cavities may be filled with a different medication solution or different concentrations of the same medication, one of which might be a priming dose to rapidly establish a given blood level of concentration followed by a sustained administration at a lower concentration. Of course, because of this construction, it is necessary that there be two filling apertures and these are shown at 52 and 54. Because the dam 50 acts as a reinforcing rib, the FIG. 6 configuration has only two reinforcing ribs 56 and, it is frequently possible to eliminate both of these ribs.

The FIG. 7 alternative construction of the housing is similar to that of FIG. 6 in that the housing is divided into two different size compartments. Housing 58 has a dam 60 dividing its interior into two compartments containing substantially ⅓ and ⅔, respectively, of the enclosed volume. Obviously other ratios and additional compartments could be created by relocation of the dam 60 or the addition of further dams. Filling apertures 62 and 64 permit the filling of the two separate compartments and reinforcing ribs 66, where used, function similarly to ribs 46 of FIG. 1. In both the FIGS. 6 and 7 embodiments, a retaining plug such as that shown at 26 in FIG. 2 is used to close and seal the filling aperture after filling.

Figure 4:
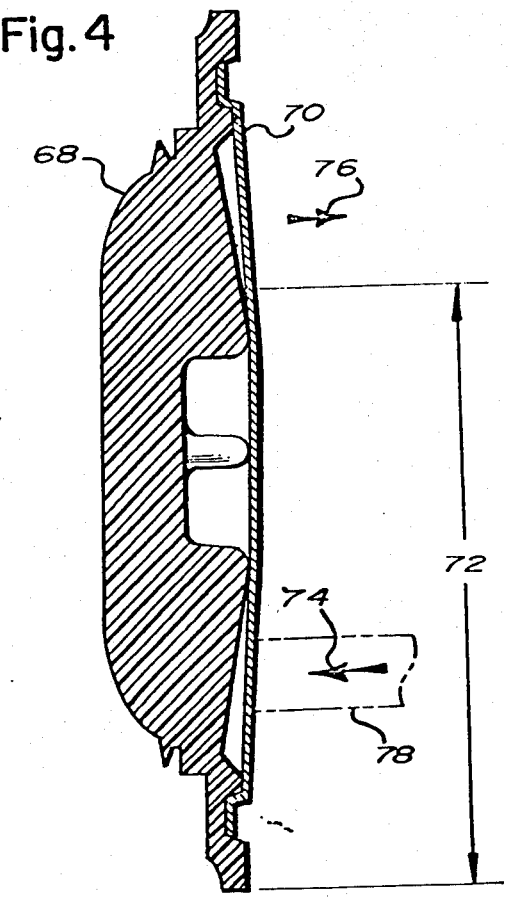
FIG. 4 is a sectional view, partially in phantom, of an alternate construction of the application cell of the invention used in combination with a filling method different from that used with the application cell of FIGS. 1–3.
Figure 5:
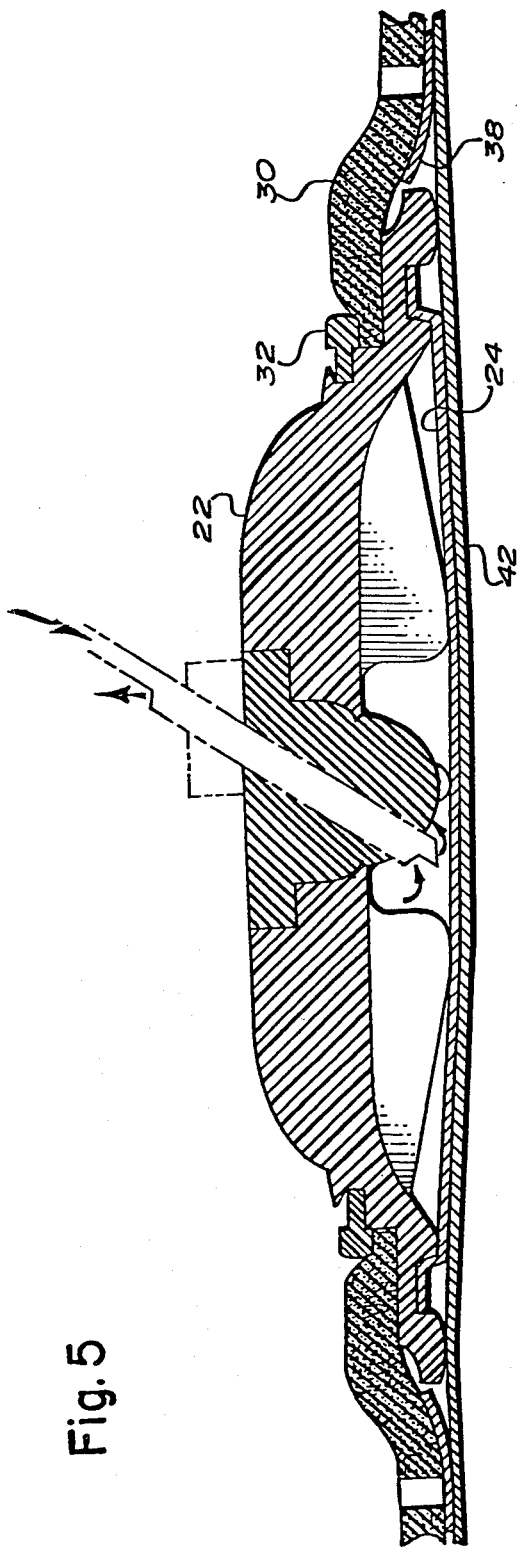
FIG. 5 is a partial section view, partially in phantom, of another alternate construction of the FIGS. 1–3 embodiment used to effect an alternate filling method.

FIGS. 4 and 5 illustrate still further alternative constructions of the cell of the invention to utilize alternative filling methods. In the FIGS. 1–3 embodiments and in the FIGS. 6 and 7 embodiments, the cell is filled by more or less conventional methods such as might be used to fill any container before a sealing closure is applied. In each of the FIGS. 4 and 5 embodiments, the filling is done in a substantially different manner after the sealing closure is applied.

In FIG. 4, the housing 68 is substantially identical to the housing 22 of FIG. 2 except that it does not contain a filling aperture. As shown, the assembly is readied for filling by heat sealing a micro-porous membrane 70 to the housing in the same manner heretofore described. The membrane 70 is then wetted with an appropriate solution over substantially ¾ of the area which covers the medication cavity as schematically indicated at 72. One appropriate solution because both inexpensive and sterile, is isopropyl alcohol. The membrane area that has been wetted is not air permeable except under fairly high pressure whereas the dry membrane is air permeable.

After wetting, a medication filling tube 78 is placed against the membrane in the wetted are and medication under pressure to move in the direction of arrow 74 applied to the exterior of membrane 70. The pressure used, while above atmospheric, is on the order of a few inches of water. Medication then passes through the micro-porous membrane to fill the container. The air inside the container is forced out past the membrane in the direction of arrow 76 by the medication displacing it until the container is full of the medication solution. With only 2–3 inches of water as a working pressure, fill times have been approximately one (1) second.

The FIG. 5 embodiment is substantially identical to that of FIG. 2 except that the filling aperture is filled with a molded in place medical grade soft rubber plug 80 in place of the plug 26. Then, filling is accomplished by means of a double hollow needle filling tool 82, one of which inserts the medication into the cell, the other permitting the escape of trapped interior air. When the tool 82 is withdrawn after filling, the plug 80 self-seals.

The foregoing has described the basic medication application cell in its several preferred embodiments. These embodiments can be used with a variety of medications since the materials of the inventive cell do not react with the great majority of medications that might be applied. The medication is ordinarily placed in a physiologically neutral or slightly stronger aqueous saline solution on the order of 0.9% to 15%, 0.9% being essentially that of the human body. As the salinity of the medication solution is increased, body fluids are increasingly attracted to the medication cell interior where they displace the cells contents; the displaced medication then migrating through the micro-porous membrane to the skin surface where it may be absorbed. The higher the medication solutions salinity, the greater the transfer rate. A bacterial inhibitor may also be added depending on the active medication employed.

The transfer rate may be decreased and shelf-life increased by the addition of glycerine to the mixture in the cell. With a 15% NaCl aqueous solution to which 15% glycerin by volume is added, shelf-life of the described embodiments is at least 3 years and the medication in the cell is transferred in about 24 hours. Increasing the glycerin level to 40% increases the transfer time to about 10 days and 50% seem to be the upper practical limit since with that concentration, transfer time is substantially 3 weeks which is the time in which the average person sloughs off the external epiderma and hence, with it, the application cell.

The foregoing description of transfer rates have been established by experimental observation. However there are many theoretical means of determining the permeability of the micro-porous diapragm or membrane including those based upon the use of Ficks laws of diffusion. Each of these, ultimately, results in a permeability constant which is an inherent characteristic of the material comprising any given medication compound and micro-porous diaphragm. The embodiments described may be used to effect these transfers and, of course, the embodiments of FIGS. 6 and 7 to effect two different rates of ministration.

The invention has been described in detail herein with particular reference to preferred embodiments thereof. However, while each of these embodiments are described, it will be understood that variations and modifications can be effected within the spirit and scope of the invention described hereinabove and as defined in the appended claims.

What is claimed is:

1. A medication container comprising medication impermeable housing means forming a generally concave shaped cavity open on one side and having flange means extending radially outward from the periphery of said cavity opening and integral with said housing means, said flange means having an annular depression therein on the side of said flange means nearest said concave cavity opening,
   medication permeable micro-porous membrane means secured in said annular depression of said flange means of said housing means and covering the open side thereof to thereby form a medication holding container permeable on one side only to the passage of medication,
   means secured to said flange means of said housing means and extending generally outwardly therefrom and adapted for adhering said medication holding container to the skin of a patient,
   strippable release sheet means secured to said skin adhering means extending radially outward from the periphery of said medication container, and
   medication impermeable vapor barrier means sealingly adhered to said release sheet means and extending over said micro-porous membrane means to thereby block exterior access to said micro-porous membrane and prevent the escape of any medication from said container.

2. In a method for filing a medication container with medication solution, said container comprising medication impermeable housing means forming a generally concave shapped cavity with a filling aperture in said cavity and having a medical grade soft rubber plug filling said filling aperture, medication permeable micro-porous membrane means secured to said housing means and covering the open side thereof to form an empty medication container, skin adhering means secured to said container for securing said container to a patient's skin and release sheet and medication impermeable vapor barrier means secured to said skin adhering means to block exterior access to said membrane, the steps of inserting a filling tool and air escape means through said soft rubber plug, applying a medication solution under pressure through said filling tool into said empty container and simultaneously expelling trapped air therefrom, and withdrawing said filling tool and air escape means from said soft rubber plug.

3. A medication container in accord with claim 1 wherein said housing means further comprises dam means dividing said concave shaped cavity into at least two separate compartments.

4. A medication container in accord with claim 3 wherein said housing means further comprises filling aperture means, one for each compartment of said housing means.

5. A medication container in accord with claim 4, further comprising retaining plug means inserted in each of said filling aperture means to sealingly close each of said filling apertures.

6. A medication container in accord with claim 5 wherein said retaining plug means comprises a molded-in-place soft rubber plug.

7. A medication container in accord with claim 1 wherein said housing means further comprises filling aperture means.

8. A medication container in accord with claim 7 further comprising retaining plug means inserted in said filling aperture means to sealingly close said filling aperture.

9. A medication container in accord with claim 8 wherein said retaining plug means comprises a molded-in-place soft rubber plug.

10. A medication container in accord with claim 1 wherein said housing means further comprises one or more reinforcing rib means integrally formed within said housing means and depending therefrom into said concave cavity for supporting said micro-porous membrane means.

11. A medication container in accord with claim 1 wherein said skin adhering means further comprises adhesive means for adhesively securing said skin adhering means to both the opposite surface of said flange means from the side with said annular depression and to the skin of a patient.

12. A medication container in accord with claim 11 further comprising retaining ring means mechanically secured to said housing means to thereby compress and secure said skin adhering means to said flange means.

13. A medication container in accord with claim 12 wherein said retaining ring means further comprises coding indicia applied thereto.

14. A medication container in accord with claim 11 wherein said skin adhering means further comprises a plurality of holes extending therethrough uniformly distributed in the area extending radially outward from said flange means.

15. A medication container in accord with claim 1 wherein said release sheet means consists of high density polethylene.

16. A medication container comprising medication impermeable housing means forming a generally concave shaped cavity open on one side, flange means extending radially outward from the periphery of said cavity opening including an annular depression therein, filling aperture means centrally located in said concave cavity and reinforcing rib means integrally formed within said housing and depending therefrom into said concave cavity, medication permeable micro-porous membrane means secured to said annular depression and covering the open side of said cavity, retaining plug means sealingly inserted in said filling aperture means, skin adhering means having a central aperture whose diameter is substantially equal to that of said cavity opening and concentric therewith, said skin adhering means being secured to said housing's flange means on the side opposite said membrane means and comprising a plurality of holes perforated in said skin adhering means in the area thereof extending radially outward from said housing flange area, strippable release sheet means having a central aperture equal to or larger in diameter than the inside flange diameter of said housing means and located concentric therewith, said release sheet means being adhesively secured to said skin adhering means, retaining ring means mechanically secured to said housing means to thereby compress and secure said skin adhering means to said housing flange means, and medication impermeable vapor barrier means sealingly adhered to said release sheet means and extending over said central aperture thereof to thereby block exterior access to said microporous membrane means and prevent the escape of any medication from said container.

17. In a medication container comprising medication impermeable housing means forming a generally concave shaped cavity open on one side, medication permeable membrane means secured to said housing and covering the open side thereof to thereby form a medication holding container permeable on one side only to the passage of medication, skin adhering means fastened to said housing means for securing said container to the skin of a patient, strippable release sheet means secured to said skin adhering means and medication impermeable vapor barrier means sealingly adhered to said release sheet means and extending over said medication permeable membrane to prevent the escape of any medication from said container, the improvement comprising, open-celled micro-porous sheet means having pore sizes smaller than bacteria size comprising said membrane means to thereby simultaneously effectuate the transfer of medication from the cell through said membrane means and prevent the passage of bacteria therethrough.

18. In a medication container comprising medication impermeable resilient housing means forming a generally concave shaped cavity open on one side, medication permeable membrane means secured to said housing means and covering the open side thereof to thereby form a medication holding container, skin adhering means fastened to said housing means for securing said container to the skin of a patient, strippable release sheet means secured to said skin adhering means and medication impermeable vapor barrier means sealingly adhered to said release sheet means and extending over said medication permeable membrane to prevent the escape of any medication from said container, the improvement comprising filling aperture means in said container means, said filling aperture means being configured to have three successively smaller diameters to form a three stepped aperture the smallest diameter being adjacent the cavity of said container means to form a resilient annular locking flange in said stepped aperture, and plug means inserted in said stepped aperture and, adapted to be locked in position therein by said resilient annular locking flange, said plug means consisting of head means and body means, said head means having a thickness and diameter to substantially completely occupy the outermost largest diameter step of said three stepped aperture means, said body means comprising, successively, a shank portion adjacent said head means, a tapered portion, a beveled locking face means and a pilot tip portion, said shank portion having a diameter to require a force fit in the center step of said three stepped aperture means, and said beveled locking face means is configured to deflect and engage said resilient annular locking flange and thereby lock said plug means in said medication container.

19. In a method for filling a medication container with medication solution, said container comprising medication impermeable housing means forming a generally concave shaped cavity and medication permeable micro-porous membrane means secured to said housing means and covering the open side thereof to form an empty medication container, the steps of applying a liquid to said micro-porous membrane over a substantial portion of said membrane area that covers the open side thereof and maintaining at least a portion of said membrane dry to thereby form wetted and unwetted areas thereof, and applying a medication solution under pressure, to a selected portion of said wetted area for the time necessary to transfer a desired amount of said medication solution into said empty cavity and simultaneously expell air from said cavity through said unwetted area.

* * * * *